(12) United States Patent
Harimoto et al.

(10) Patent No.: US 12,115,058 B2
(45) Date of Patent: Oct. 15, 2024

(54) NERVE REGENERATION-INDUCING TUBE

(71) Applicant: TORAY INDUSTRIES, INC., Tokyo (JP)

(72) Inventors: Kenichi Harimoto, Shiga (JP); Hirokazu Sakaguchi, Shiga (JP); Satoshi Yamada, Shiga (JP)

(73) Assignee: TORAY INDUSTRIES, INC., Tokyo (JP)

( * ) Notice: Subject to any disclaimer, the term of this patent is extended or adjusted under 35 U.S.C. 154(b) by 721 days.

(21) Appl. No.: 17/431,295

(22) PCT Filed: Feb. 14, 2020

(86) PCT No.: PCT/JP2020/005783
§ 371 (c)(1),
(2) Date: Aug. 16, 2021

(87) PCT Pub. No.: WO2020/170961
PCT Pub. Date: Aug. 27, 2020

(65) Prior Publication Data
US 2022/0125569 A1 Apr. 28, 2022

(30) Foreign Application Priority Data
Feb. 22, 2019 (JP) .................................. 2019-030990

(51) Int. Cl.
*A61L 27/38* (2006.01)
*A61F 2/02* (2006.01)
*A61F 2/06* (2013.01)

(52) U.S. Cl.
CPC ........ *A61F 2/02* (2013.01); *A61F 2210/0004* (2013.01)

(58) Field of Classification Search
CPC ...... A61F 2/04; A61F 2/02; A61F 2/82; A61F 2/06; A61F 2210/0004; A61F 2002/30062;
(Continued)

(56) References Cited

U.S. PATENT DOCUMENTS 4,534,349 A * 8/1985 Barrows ................. A61L 27/50
606/154
4,870,966 A * 10/1989 Dellon ................ A61B 17/1128
606/154
(Continued)

FOREIGN PATENT DOCUMENTS

| JP | 2005-237476 A | 9/2005 |
| JP | 2009-524507 A | 7/2009 |

(Continued)

OTHER PUBLICATIONS

International Search Report, issued in PCT/JP2020/005783, PCT/ISA/210, dated Apr. 21, 2020.
(Continued)

*Primary Examiner* — Seema Mathew
(74) *Attorney, Agent, or Firm* — Birch, Stewart, Kolasch & Birch, LLP

(57) ABSTRACT

A nerve regeneration-inducing tube includes a cylindrical body, and a plurality of fibers that are housed in the body and extend in a longitudinal direction of the body. At least a part of the fibers is a modified cross-section fiber that has an axis extending in a longitudinal direction of the fibers, and at least three protrusions that continue in the longitudinal direction of the fibers, protrude from the axis, and have a height of 0.5 μm or more from the axis.

7 Claims, 8 Drawing Sheets

(58) Field of Classification Search
CPC .... A61F 2/0077; A61L 2430/32; A61L 27/58; A61L 31/148; A61L 27/3878; A61L 27/383; A61B 17/1128
See application file for complete search history.

(56) References Cited

U.S. PATENT DOCUMENTS

| | | | | | |
|---|---|---|---|---|---|
| 4,877,029 | A | * | 10/1989 | Valentini | A61L 31/04 606/152 |
| 5,011,486 | A | * | 4/1991 | Aebischer | A61L 31/146 600/152 |
| 5,024,671 | A | * | 6/1991 | Tu | A61F 2/06 623/1.42 |
| 5,030,225 | A | * | 7/1991 | Aebischer | A61L 31/14 606/152 |
| 5,676,699 | A | * | 10/1997 | Gogolewski | A61L 31/148 623/16.11 |
| 6,031,148 | A | * | 2/2000 | Hayes | A61F 2/0077 606/154 |
| 6,214,021 | B1 | * | 4/2001 | Hadlock | A61B 17/1128 606/152 |
| 6,958,158 | B2 | | 10/2005 | TenHuisen | A61P 37/00 604/93.01 |
| 7,084,082 | B1 | * | 8/2006 | Shimizu | A61L 26/0033 424/443 |
| 8,475,536 | B2 | * | 7/2013 | Tong | A61F 2/30767 623/23.57 |
| 9,821,501 | B2 | * | 11/2017 | Fujimura | B29C 48/09 |
| 11,596,922 | B2 | * | 3/2023 | Fujieda | B01J 20/28083 |
| 11,850,310 | B2 | * | 12/2023 | Shelton, IV | A61B 17/07292 |
| 11,957,815 | B2 | * | 4/2024 | Datt | A61L 27/54 |
| 2003/0060871 | A1 | * | 3/2003 | Hill | A61L 31/146 623/1.42 |
| 2003/0140790 | A1 | * | 7/2003 | Herczeg | B01D 65/08 96/10 |
| 2007/0010831 | A1 | * | 1/2007 | Romero-Ortega | A61B 17/1128 606/152 |
| 2007/0269481 | A1 | | 11/2007 | Li et al. | |
| 2009/0060961 | A1 | * | 3/2009 | Naruse | C08J 9/36 428/401 |
| 2010/0168720 | A1 | * | 7/2010 | Swain | A61F 13/00063 514/6.9 |
| 2017/0333871 | A1 | * | 11/2017 | Fujieda | B01J 20/261 |
| 2019/0126239 | A1 | * | 5/2019 | Fujieda | A61M 1/36 |
| 2020/0138439 | A1 | * | 5/2020 | Dosta | A61L 27/16 |

FOREIGN PATENT DOCUMENTS

| | | | |
|---|---|---|---|
| JP | 2012-161508 A | 8/2012 | |
| JP | 2012-250069 A | 12/2012 | |
| WO | WO-2016067967 A1 * | 5/2016 | .......... A61M 1/3679 |
| WO | WO-2017188110 A1 * | 11/2017 | .......... A61M 1/0259 |

OTHER PUBLICATIONS

Written Opinion of the International Searching Authority, issued in PCT/JP2020/005783, PCT/ISA/237, dated Apr. 21, 2020.

Japanese Office Action for corresponding Japanese Application No. 2020-511407, dated Oct. 31, 2023, with English translation.

* cited by examiner

NERVE REGENERATION-INDUCING TUBE

FIELD

The present invention relates to a nerve regeneration-inducing tube.

BACKGROUND

As a medical device for inducing nerve regeneration and curing an injured area that is formed between a central side and a peripheral side of nervous tissues, a nerve regeneration-inducing tube has been conventionally known. Use of the nerve regeneration-inducing tube suppresses entry of a connective tissue to be a disorder of nerve regeneration into the injured area.

FIG. 15 is a view illustrating a use example of a conventional nerve regeneration-inducing tube. On one end side of a nerve regeneration-inducing tube 300 illustrated in FIG. 15, nerve cells 200 and Schwann cells 210 are disposed. In the inside of the nerve regeneration-inducing tube 300, Schwann cells 211 proliferate. In the inside of the proliferated Schwann cells 211, an axon 201 extends. At this time, entry of a connective tissue is suppressed by the nerve regeneration-inducing tube 300, and therefore inhibition of a route where the axon. 201 extends is suppressed. Thus, nerve regeneration using the nerve regeneration-inducing tube 300 is promoted.

In nerve regeneration, efficient entry of the axon 201 and the Schwann cells 211 into the nerve regeneration-inducing tube 300 is important for promotion of nerve regeneration. In particular, as the nerve regeneration-inducing tube 300 is longer, the Schwann cells 211 more easily adhere to the inside of the tube. Therefore, it is important that the axon 201 rapidly and linearly extends in the tube. As a technique for promoting nerve regeneration, a technique in which a bundle of fibers extending in a longitudinal direction of a nerve regeneration-inducing tube is disposed in the nerve regeneration-inducing tube is known (for example, see Patent Literature 1). In Patent Literature 1, the bundle of fibers is a scaffold for adhering Schwann cells, and guides extension of an axon is the tube.

CITATION LIST

Patent Literature

Patent Literature 1: Japanese Patent application Laid-open No. 2005-237476

SUMMARY

Technical Problem

For achieving further efficiency of nerve regeneration, a technique for further improving an extension rate of an axon is required.

The present invention is made in view of the circumstances, and an object of the present invention, is to provide a nerve regeneration-inducing tube capable of improving the extension rate of an axon.

Solution to Problem

In order to solve the problem described above, a nerve regeneration-inducing tube according to the present invention includes: a cylindrical body; and a plurality of fibers that are housed in the body and extend in a longitudinal direction of the body. At least a part of the fibers is a modified cross-section fiber that has an axis extending in a longitudinal direction of the fibers, and at least three protrusions that continue in the longitudinal direction f the fibers, protrude from the axis, and have a height of 0.5 μm or more from the axis.

In the nerve regeneration-inducing tube according to the present invention, in a cross section of the modified cross-section fiber, a modification degree that is a ratio of a diameter of a circle circumscribed to the cross section to a diameter of a circle inscribed to the cross section is 1.5 to 12.0.

In the nerve regeneration-inducing tube according to the present invention, the protrusions have a height of 1.0 μm or more.

In the nerve regeneration-inducing tube according to the present invention, the modified cross-section fiber has 10 or less of the protrusions.

In the nerve regeneration-inducing tube according to the present invention, the modified cross-section fiber has a Y-cross-section fiber having three of the protrusions or an X-cross-section fiber having four of the protrusions.

In the nerve regeneration-inducing tube according to the present invention, the fibers include fibers having different cross-sectional shapes.

In the nerve regeneration-inducing tube according to the present invention, at least one of the body and the fibers includes a bioabsorbable polymer.

Advantageous Effects of Invention

The nerve regeneration-inducing tube of the present invention exerts effects of improving migration of Schwann cells and an axon extension rate, and linearly extending an axon extension direction to achieve efficient nerve regeneration.

DESCRIPTION OF EMBODIMENTS

Figure 1:
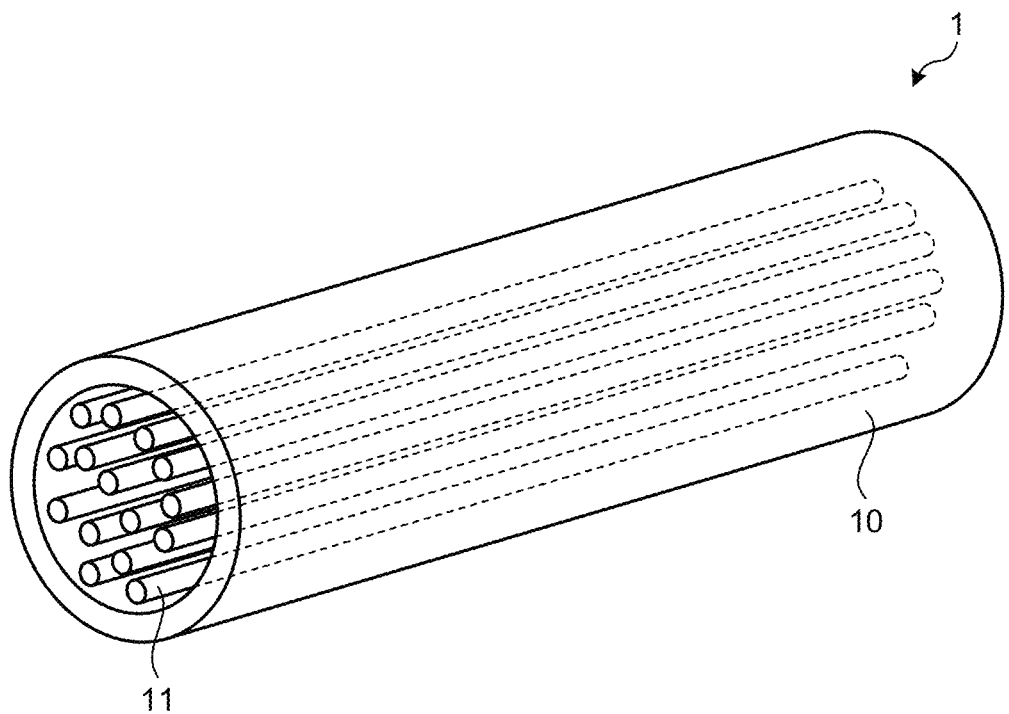
FIG. 1 is a perspective view schematically illustrating a nerve regeneration-inducing tube according to one embodiment of the present invention.

Hereinafter, an aspect for carrying out the present invention will be described in detail with the drawings. The present invention is not limited to the following embodiments. Description about definitions, preferred aspects, and variations in the description of the embodiments may be interpreted as descriptions of nerve regeneration tube of the present invention as a generic concept so as to be easily understood by one skilled in the art. The drawings referred to in the following description only schematically illustrate shapes, sizes, and positional relations enough to understand the content of the present invention. Therefore, the sizes, shapes, and positional relations of the present invention are not limited to those exemplified in the drawings. In the description of the drawings, the same portions are denoted with the same reference symbols.

Embodiment

A nerve regeneration-inducing tube according to an embodiment of the present invention will be described with reference to FIGS. 1 to 3. FIG. 1 is a perspective view schematically illustrating the nerve regeneration-inducing tube according to the embodiment of the present invention. A nerve regeneration-inducing tube 1 illustrated in FIG. 1 includes a cylindrical body 10, and modified cross-section fibers 11 (or 11A) that are provided inside the body 10 and extend in a central axis direction of the body 10.

The body 10 is formed using a bioabsorbable material. For example, the body 10 is a cylinder having an outer circumferential diameter of 0.5 mm or more and 4.0 mm or less. The thickness of the body 10 can be appropriately adjusted according to the use mode. The bioabsorbable material is a biodegradable material that is degraded by an acid, an alkali, or an enzyme, and in which a degradation product thereof disappears in the body by metabolism, elimination, and the like. A bioabsorbable polymer is a polymer that is derived from an organism or is artificially synthesized in the bioabsorbable material. Examples thereof include a protein or a derivative thereof such as collagen or gelatin, a polysaccharide or a derivative thereof such as chitosan, a copolymer of one or more kinds of monomers selected from lactic acid, glycolic acid, and caprolactone, and an aliphatic polyester such as a lactide polymer. It is preferable that the body be porous, so that the body fluid infiltrate into the body, and that a substance can be exchanged between the inner side and the outer side.

The modified cross-section fibers 11 (or 11A) are fibrous and extend in the longitudinal direction of the body 10. A cross section that is the cross section of the modified cross-section fibers 11, and is a section as a plane orthogonal to the longitudinal direction, has an irregular shape that differs from a circle and an ellipse. The modified cross-section fibers 11 (or 11A) are formed using the bioabsorbable material.

Figure 2:
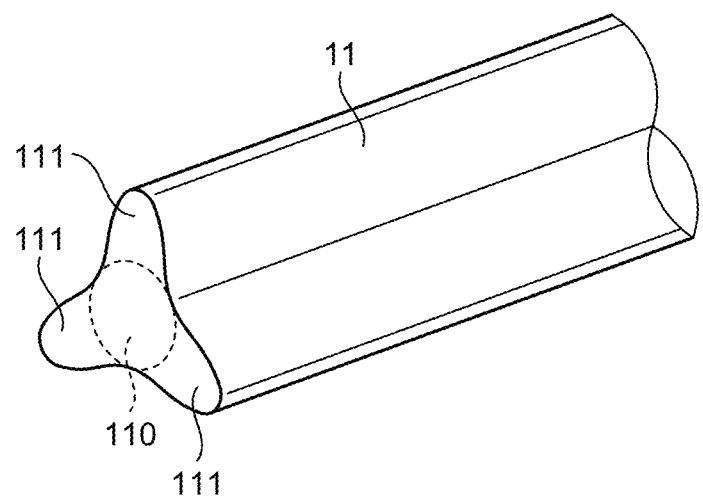
FIG. 2 is a perspective view illustrating one example of a modified cross-section fiber housed in the nerve regeneration-inducing tube according to the embodiment of the present invention.
Figure 3:
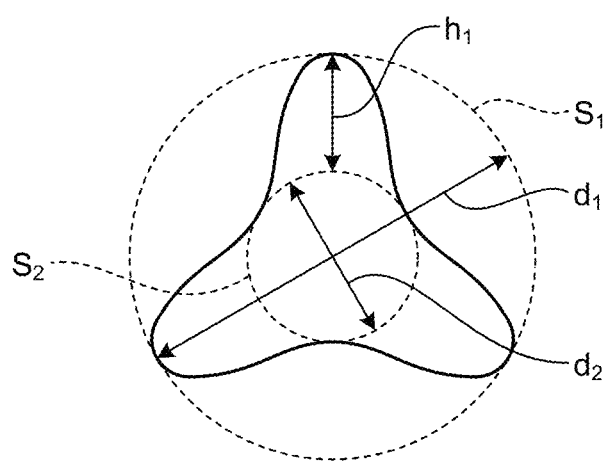
FIG. 3 is a view illustrating a cross section of the modified cross-section fiber illustrated in FIG. 2.

FIG. 2 is a perspective view illustrating one example of the modified cross-section fibers housed in the nerve regeneration-inducing tube according to the embodiment of the present invention. FIG. 3 is a view illustrating a cross section of the modified cross-section fiber illustrated in FIG. 2. The modified cross-section fibers 11 illustrated in FIG. 2 each include a cylindrical axis 110, and three protrusions 111 protruding from the axis. The three protrusions 111 protrude in directions that are different from each other with respect to the axis 110. The modified cross-section fibers 11 are a Y cross-section fiber in which the cross section that is a section as a plane orthogonal to the longitudinal direction has a substantially Y shape. The Y shape herein referred to may be a shape having 120° (240°, and 360°)-rotation symmetry in which the angles between the adjacent protrusions 111 are the same, or a shape having no rotation symmetry except for 360°-rotation symmetry in which the angles are not the same as each other.

Due to the presence of the protrusions, the surface area of the fibers is increased. The protrusions become an obstacle, and a space is formed between the fibers. Thus, a region where Schwann cells and an axon can adhere on the fibers can be increased. In order to suppress a decrease of the region where the cells and the axon adhere when the fibers are bundled and placed resulting in adhesion of the fibers, it is preferable that the number of the protrusions be three or more, and it is more preferable that two or more kinds of fibers having different protrusions be mixed. In this case, it is further preferable that a circular fiber and a fiber having a protrusion be mixed.

The height of each of the protrusions 111 is 0.5 μm or more, and preferably 1.0 μm or more, with respect to the axis 110. Herein, the height of the protrusions 111 is the longest distance (for example, a height $h_1$ in FIG. 3) among distances in a direction orthogonal to a tangent line of an inscribed circle that is inscribed to the cross section of the fibers between the tangent line and an external edge of the cross section of the fibers. In this embodiment, the external form of the axis 110 in the cross section of the fibers corresponds to the inscribed circle of the cross section of the fibers.

In the modified cross-section fibers 11, the modification degree that is determined as a ratio ($d_1/d_2$) of the diameter $d_1$ of a circle $S_1$ circumscribed to the cross section that is a section as a plane orthogonal to the longitudinal direction, to the diameter $d_2$ of a circle $S_2$ inscribed to the cross section is 1.5 or more and 12.0 or less. The diameters d1 and the diameters d2 of 20 fibers randomly extracted from an image obtained by photographing a fiber cross section by an electron microscope are measured and averaged. From the average, the modification degree can be calculated.

Figure 4:
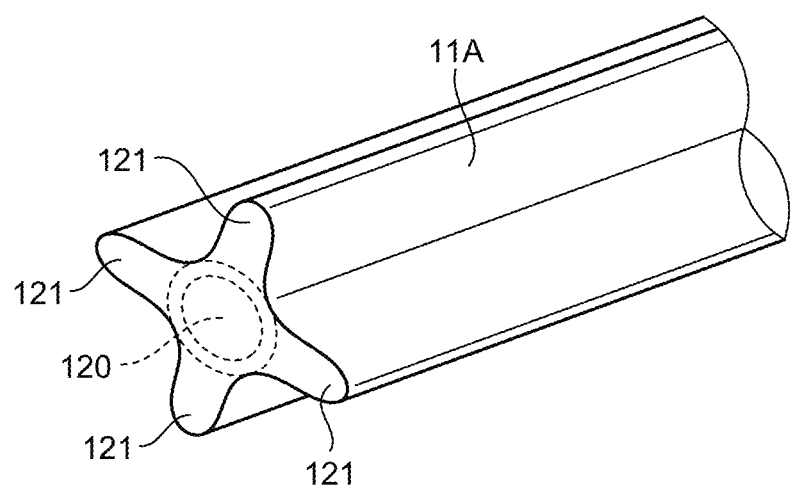
FIG. 4 is a perspective view illustrating another example of the modified cross-section fiber housed in the nerve regeneration-inducing tube according to the embodiment of the present invention.
Figure 5:
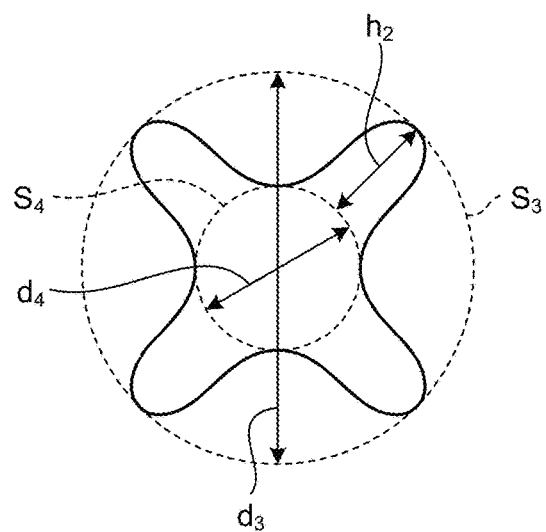
FIG. 5 is a view illustrating a cross section of the modified cross-section fiber illustrated in FIG. 4.

FIG. 4 is a perspective view illustrating another example of the modified cross-section fibers housed in the nerve regeneration-inducing tube according to the embodiment of the present invention. FIG. 5 is a view illustrating a cross section of the modified cross-section fiber illustrated in FIG. 4. The modified cross-section fibers 11A illustrated in FIG. 4 each include a cylindrical axis 120, and four protrusions 121 protruding from the axis. The four protrusions 121 protrude in directions that are different from each other with respect to the axis 120. The modified cross-section fibers 11A are an X cross section fiber in which the cross section has a substantially X shape. The X shape herein referred to may be a shape having 90° (180°, 270°, and 360°)-rotation symmetry in which the angles between the adjacent protrusions 121 are the same, or a shape having no rotation symmetry except for 360°-rotation symmetry in which the angles are not the same as each other.

The height of each of the protrusions 121 is 0.5 μm or more, and preferably 1.0 or more, with respect to the axis 120. Herein, the height of the protrusions 121 is the longest distance (for example, a height $h_2$ in FIG. 5) among distances in a direction orthogonal to a tangent line of an inscribed circle that is inscribed to the cross section between the tangent line and an external edge of the cross section of the fibers. In this embodiment, the external form of the axis 120 in the cross section of the fibers corresponds to the inscribed circle of the cross section of the fibers.

In the modified cross-section fibers 11A, the modification degree that is determined as a ratio ($d_3/d_4$) of the diameter $d_3$ of a circle $S_3$ circumscribed to the cross section that is a section as a plane orthogonal to the longitudinal direction, to the diameter $d_4$ of a circle $S_4$ inscribed to the cross section is 1.5 or more and 12.0 or less.

As the modification degree is larger, the surface area of the fibers is larger, the space formed when the fibers are bundled is also larger, and Schwann cells and an axon more easily enter into the inside of the tube. Therefore, the modification degree is preferably 1.5 or more. As the modification degree is too large, the protrusions are likely to be crashed due to bending. Therefore, the modification degree is preferably 12.0 or less.

Additionally, modified cross-section fibers having 10 or less protrusions in a cross section can be disposed.

On the body 10, one kind of the modified cross-section fibers 11 or 11A, or the modified cross-section fibers having 10 or less protrusions is provided alone, or two kinds or more of fibers having different cross section shapes are provided in combination so that the number of the fibers falls within a range of 5 or more and 500,000 or less.

The modified cross-section fibers may be housed in the body 10 in combination with conventional circular or elliptical fibers. Specifically, for the nerve regeneration-inducing tube 1 according to the present embodiment, the aforementioned modified cross-section fibers are employed in at least a part of fibers.

Figure 6:
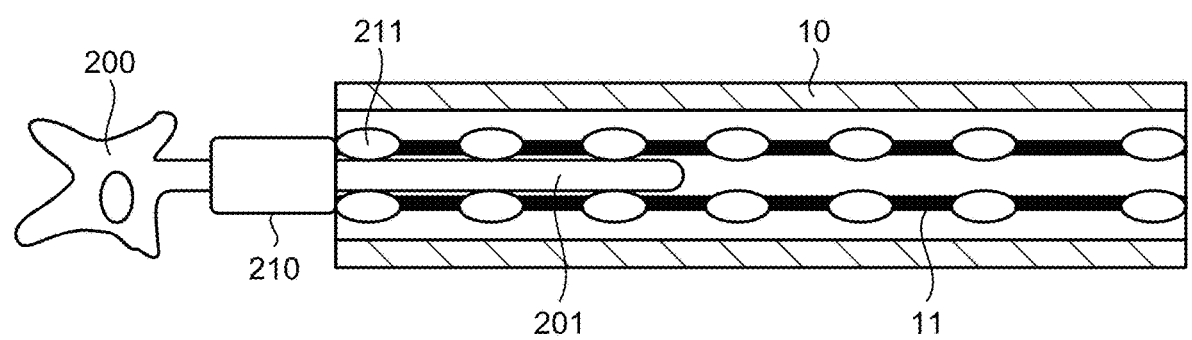
FIG. 6 is a view illustrating a use example of the nerve regeneration-inducing tube according to the embodiment of the present invention.

FIG. 6 is a view illustrating a use example of the nerve regeneration-inducing tube according to the embodiment of the present invention. When on an end side of the nerve regeneration-inducing tube 1, nerve cells 200 and Schwann cells 210 are disposed, Schwann cells 211 move toward a deep portion in the inside of the tube and proliferate. In the inside of the Schwann cells 211 disposed in the tube, an axon 201 extends. When the modified cross-section fibers are used at this time, the extension of the axon 201 is improved. Thus, nerve regeneration using the nerve regeneration-inducing tube 1 is promoted.

In the aforementioned embodiment, the nerve regeneration-inducing tube 1 includes the cylindrical body 10, and the protrusions 111 (or 121) that are provided inside the body 10 and have a height of 0.5 μm or more with respect to the axis 110 (or 120). According to the embodiment, the surface area for migrating Schwann cells can be increased by use of the modified cross-section fibers. When the nerve regeneration-inducing tube 1 according to the embodiment is used for nerve regeneration, the extension of an axon can be improved, and efficient nerve regeneration can be achieved.

Experimental Examples

Hereinafter, Experimental Examples for evaluations of adhesion of Schwann cells and extension of an axon will be described. The present invention is not interpreted to be limited by the Experimental Examples.

[Preparation of Sample]

Figure 7:
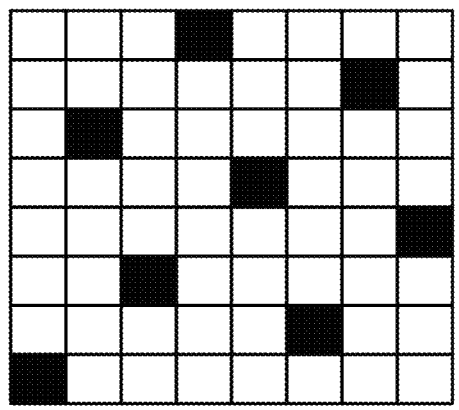
FIG. 7 is a view illustrating a weave diagram of a weave structure used in Experimental Examples.

In all Experimental Examples and Comparative Experimental Examples, a circular cross-section fiber having a single-yarn diameter of 14.7 μm was used as a warp, and the warp density was adjusted so as to be the same. As a weft, yarns listed in Table 1 were used. In a weave condition, the common weave structure was an 8-harness satin weave structure, and the weft density was adjusted so that the weft cover factor (hereinafter referred to as weft CF) of each weft in Table 1 was 1,300. Thus, a fabric sample was prepared. FIG. 7 is a view illustrating a weave diagram of the weave structure used in Experimental Examples. In Experimental Examples, the 8-harness satin weave structure illustrated in the weave diagram of FIG. 7 was employed.

Herein, the weft CF is calculated from the following formula.

$$\text{Weft CF} = \sqrt{A} \times N$$

A: Weft fineness (dtex)
N: Number of weft (yarns/2.54 cm)

The prepared fabric sample was punched by a punch with a diameter of 15 mm, to obtain a circular fabric piece. The obtained fabric piece was immersed in 99.5% ethanol (available from FUJIFILM Wako Pure Chemical. Corporation) for about 10 minutes, resulting in sterilization, and then air-dried in a safety cabinet. Subsequently, the fabric piece was immersed in an atelocollagen solution (available from KOKEN) prepared in 100 μg/mL for 30 minutes, and then air-dried in a safety cabinet. For evaluations of axon growth rate and linear extension, the fabric piece was further immersed in a rat-derived laminin (available from Sigma) aqueous solution prepared in 50 μg/mL for 2 hours, and then air-dried in a safety cabinet. Next, the fabric piece was set in one well of a 24-well plate (available from Thermofisher), and sterilized by an autoclave, and a cylindrical metal tool having an outer diameter of 14 mm, an inner diameter of 12 mm, and a height of 10 mm was placed as a weight. For each sample, three wells were prepared. The following items at n=3 were evaluated,

TABLE 1

|  | Weft | | | | | Weave condition | |
| --- | --- | --- | --- | --- | --- | --- | --- |
|  | Single-yarn diameter (μm) | Cross section shape | Modification degree | Height of protrusion (μm) | Number of protrusions of 0.5 μm or more | Weave structure | Weft CF |
| Experimental Example 1 | 14.7 | Substantially Y shape | 1.89 ± 0.071 | 0.78 ± 0.21 | 3 | 8-harness satin | 1300 |
| Experimental | 15.9 | Substantially | 2.56 ± 0.57 | 1.25 ± 0.22 | 4 | 8-harness | 1300 |

TABLE 1-continued

| | Weft | | | | | |
|---|---|---|---|---|---|---|
| | Single-yarn | | | | Weave condition | |
| | diameter (μm) | Cross section shape | Modification degree | Height of protrusion (μm) | Number of protrusions of 0.5 μm or more | Weave structure | Weft CF |
| Example 2 | | X shape | | | | satin | |
| Comparative Experimental Example 1 | 10.4 | Circle | 1 | 0 | 0 | 8-harness satin | 1300 |
| Comparative Experimental Example 2 | 12.7 | Substantially elliptical shape | 1.73 ± 0.070 | 0.85 ± 0.23 | 2 | 8-harness satin | 1300 |

Experimental Example 1

Figure 8:
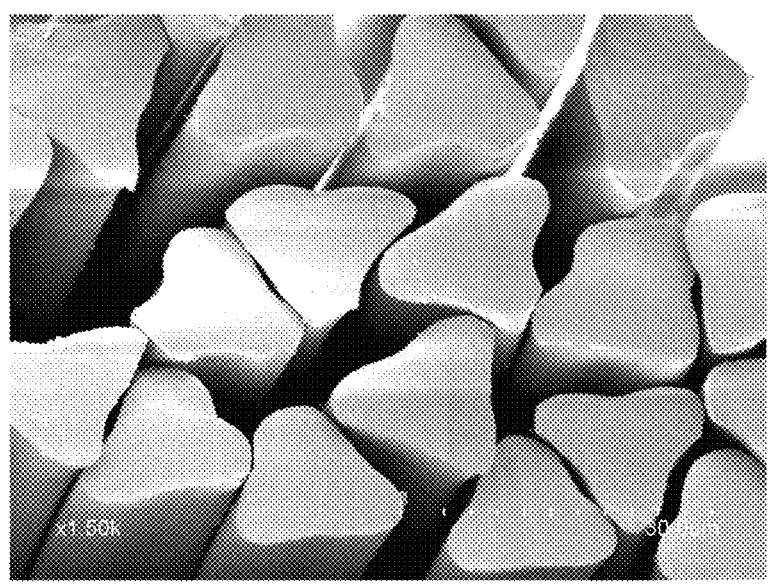
FIG. 8 is a view illustrating cross sections of modified cross-section fibers in Experimental Example 1.

FIG. 8 a view illustrating cross sections of modified cross-section fibers in Experimental Example 1. In Experimental Example 1, modified cross-section fibers including three protrusions and having a substantially Y shaped cross section as illustrated FIG. 8 were used as a weft, and each evaluation was performed.

Experimental Example 2

Figure 9:
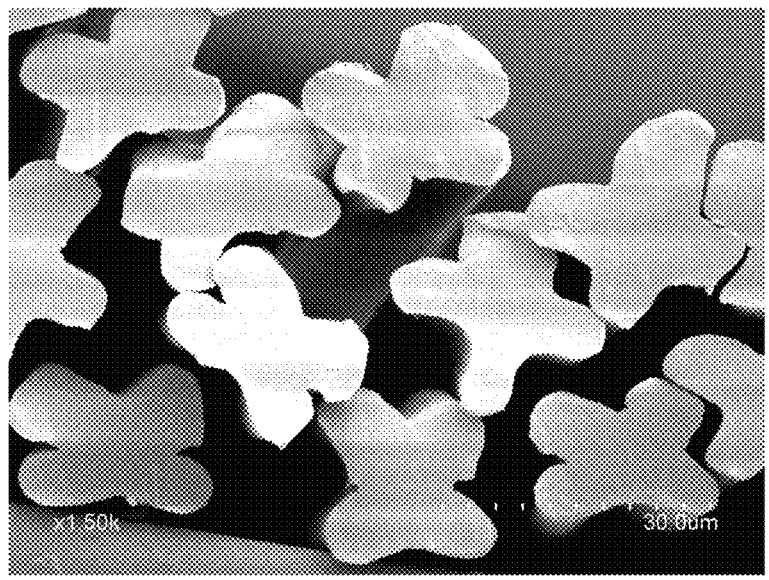
FIG. 9 is a view illustrating cross sections of modified cross-section fibers in Experimental Example 2.

FIG. 9 is a view illustrating cross sections of modified cross-section fibers in Experimental Example 2. In Experimental Example 2, modified cross-section including four protrusions and having a substantially X-shaped cross section as illustrated FIG. 9 were used as a weft, and each evaluation was performed.

Comparative Experimental Example 1

In Comparative Experimental Example 1, fibers having a perfect circular cross section were used as a weft, and each evaluation was performed.

Comparative Experimental Example 2

Figure 10:
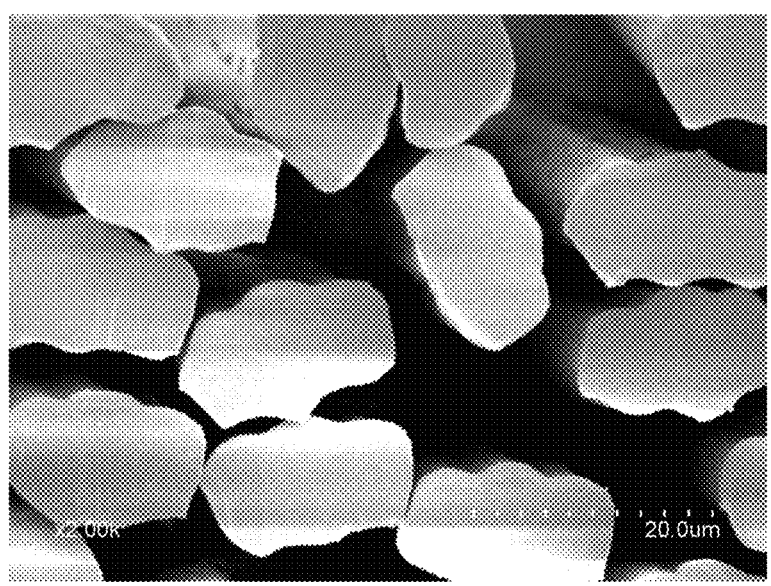
FIG. 10 is a view illustrating cross sections of modified cross-section fibers in Comparative Experimental Example 2.

FIG. 10 is a view illustrating cross sections of modified cross-section fibers in Comparative Experimental Example 2. In Comparative Experimental Example 2, modified cross-section fibers including two protrusions of 0.5 μm or more and about two protrusions of less than 0.5 μm, and having a substantially ellipsoid shape as illustrated in FIG. 10 were used as a weft, and each evaluation was performed.

[Evaluation of Cell Adhesion]

Figure 11:
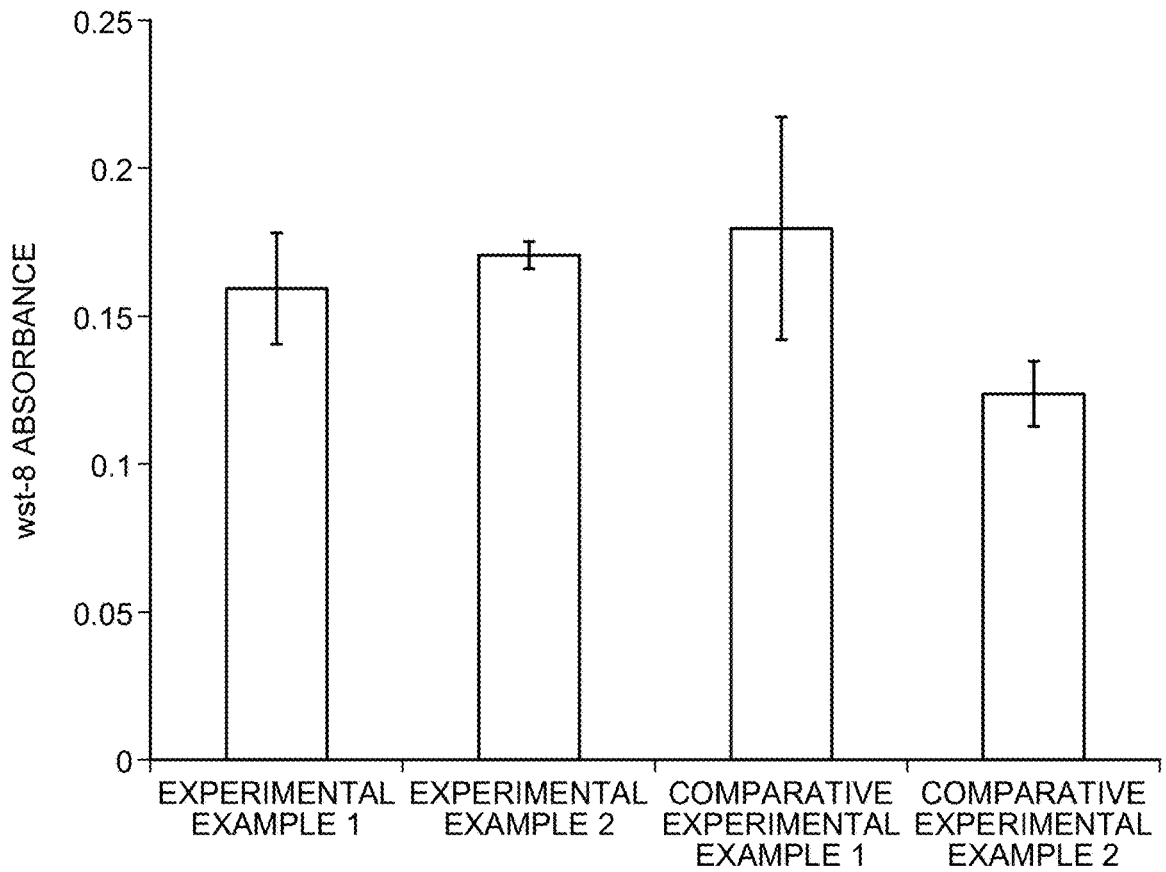
FIG. 11 is a graph illustrating results of cell adhesion evaluation.

IMS32 (available from Cosmo Bio Co., Ltd.) as Schwann cells was suspended in a culture medium for IMS32 (available from. Cosmo Bio Co., Ltd.), inoculated at 125,000 cells/1 mL/well, and cultured at 37° C. and a saturated vapor pressure in a 5% $CO_2$ atmosphere for 24 hours. Subsequently, the number of cells was measured by Cell Counting Kit (available from DOJINDO LABORATORIES). Specifically, a solution in which 10% WST-8 was added to the culture medium for IMS was prepared, and 1 mL of the solution was added to a well in which a culture supernatant had been removed. The cells were cultured at 37° C. and a saturated vapor pressure in a 5% $CO_2$ atmosphere for 1 hour, 100 μL of culture supernatant was collected in each well of a 96-well plate, and the absorbance at 480 nm was measured by a microplate reader (SpectraMax M5 available from Molecular devices). FIG. 11 illustrates the results measured in Experimental Examples. FIG. 11 is a graph illustrating the results of cell adhesion evaluation. As can be understood from FIG. 11, it can be said that the number of Schwann cells adhering to the modified cross-section fibers having a substantially Y- or X-shaped cross section is equivalent to the number of Schwann cells adhering to the fibers having a circular cross section, but is more than the number of Schwann cells adhering to the fibers having a substantially elliptical cross section.

[Evaluation of Neurite (Outgrowth]

Cells of PC12 (available from DS Pharma Biomedical Co., Ltd.) were suspended in an RPMI culture medium supplemented with 1% house serum (available from Funakoshi Co., Ltd.) and 100 ng/mL NGF (available from Cosmo Bio Co., Ltd.), and inoculated at 1,000 cells/1 mL/well. The cells were cultured at 37° C. and a saturated vapor pressure in a 5% $CO_2$ atmosphere, and the culture medium was exchanged at an interval of 3 or 4 days.

On the 14th day, the supernatant was removed, and 1 mL of a 4% paraformaldehyde phosphate buffer solution (available from FUJIFILM Wako Pure Chemical Corporation) was then added. The mixture was allowed to stand for 10 minutes, the supernatant was removed, and 1 mL of PBS(−) (available from FUJIFILM Wako Pure Chemical Corporation) was injected and removed three times for cleaning. Subsequently, 1 mL of a Giemsa staining solution (available from FUJIFILM Wako Pure Chemical Corporation) prepared in 2% was added, the mixture was allowed to stand for 10 minutes, and the supernatant was removed. Thereafter, 1 mL of pure water was injected and removed three times for cleaning, and the culture was air-dried.

Figure 12:
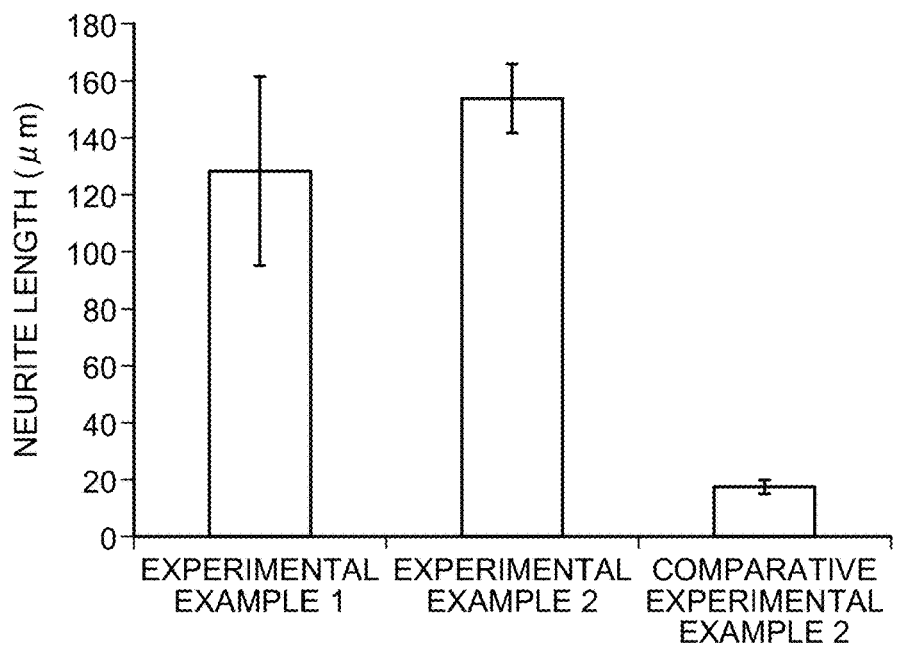
FIG. 12 is a graph illustrating results of neurite outgrowth evaluation.

The stained fabric piece sample was photographed by a microscope (KH-1300 available from Hirox Co., Ltd.). As the length of an elongate projection extending from a cell body, a direct distance between a cell nucleus and a point where a tip of the projection reached was measured by bundled image processing software (2DMesure). FIG. 12 illustrates the results measured in Experimental Examples. FIG. 12 is a graph illustrating the results of neurite outgrowth evaluation. As can be understood from FIG. 12, it can be said that the neurite length in a case of the modified cross-section fibers having a substantially Y- or X-shaped cross section is longer than that in a case of the fibers having a substantially elliptical shape cross section.

[Evaluation of Axon Growth Rate and Linear Extension]

Dorsal root ganglia (DRG) obtained from the spinal cord of rat fetus with 14 days old were suspended in a Neuro Medium-A culture medium (available from Gibco) supplemented with 100 ng/mL of NGF (available from Cosmo Bio Co., Ltd.), and each inoculated in each well of a well plate.

The DRG was cultured at 37° C. and a saturated vapor pressure in a 5% $CO_2$ atmosphere for 4 days.

Four days after initiation of cultivation, the supernatant was removed, and 1 mL of a 4% paraformaldehyde phosphate buffer solution (available from FUJIFILM Wako Pure Chemical Corporation) was then added. The mixture was allowed to stand for 10 minutes, the supernatant was removed, and 1 ml of PBS(-) (available from FUJIFILM Wako Pure Chemical Corporation) was injected and removed three times for cleaning. Subsequently, the DPG was immersed in a blocking solution. (Blocking One: available from NACATAT TESQUE, INC.) overnight, and 1 mL of PBS(-) (available from FUJIFILM Wako Pure Chemical Corporation) was injected and removed three times for cleaning. Next, the DRG was labeled with anti-β tubulin mouse antibody (available from Promega Corporation), and stained by an ALKALINE PHOSPHATASE staining kit (available from Vector Laboratory). After staining, a stained region was photographed by a fluorescent microscope (available from Olympus Corporation). A liner extension distance (μm) between a center of the DRG and a point where an axon reached was measured by an image analysis software (ImageJ). The axon growth rate was determined by dividing the liner extension distance by the number of cultivation days. The long axis and the short axis of an area where the axon extended were measured, and the aspect ratio obtained by dividing the long axis by the short axis was an indication of linear extension evaluation.

Figure 13:
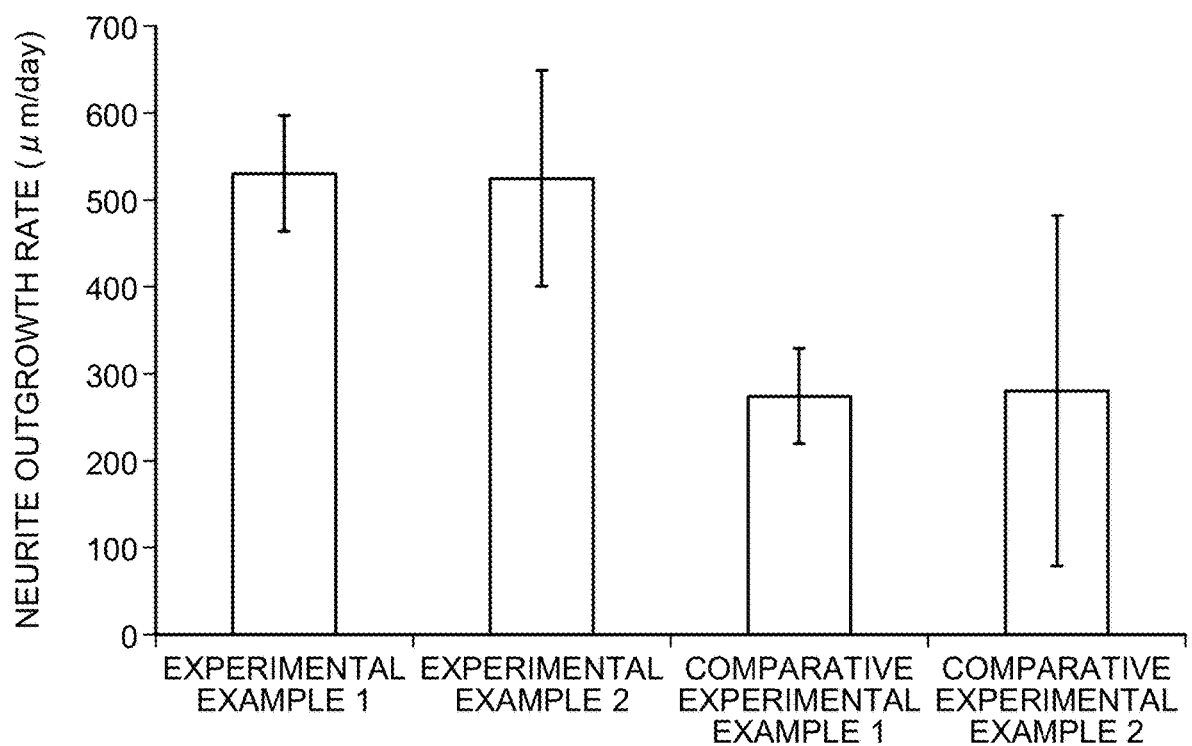
FIG. 13 is a graph illustrating results of axon growth rate evaluation (neurite outgrowth rate).
Figure 14:
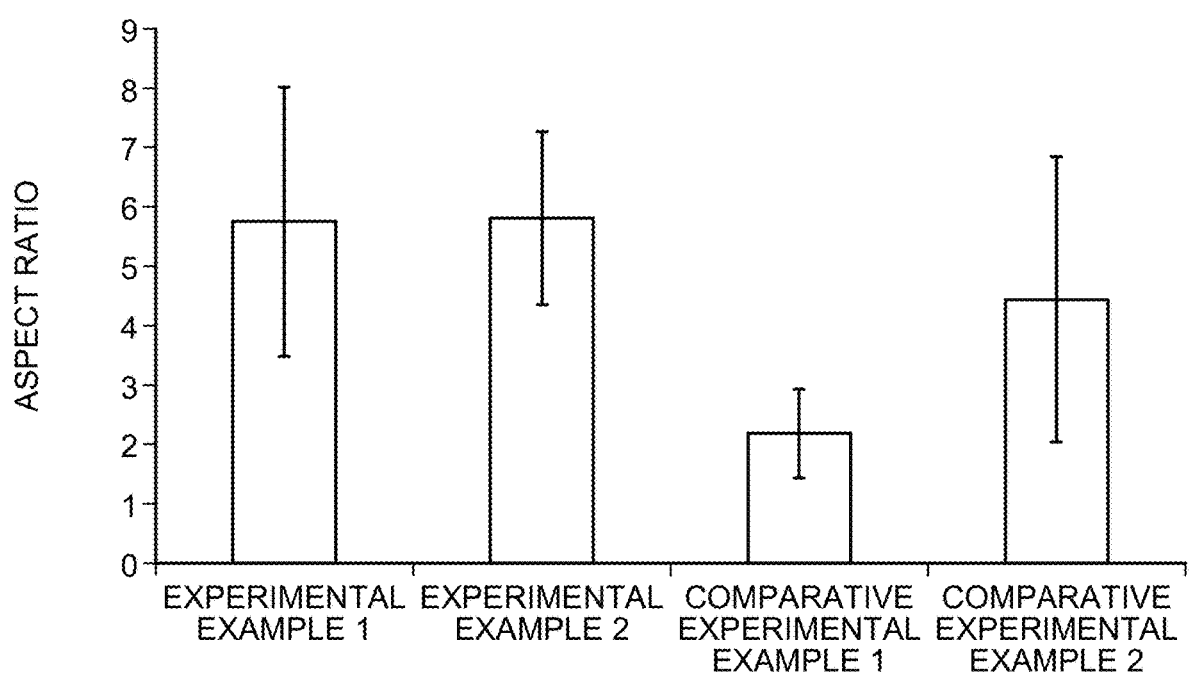
FIG. 14 is a graph illustrating results of axon growth linear extension evaluation (aspect ratio).
Figure 15:
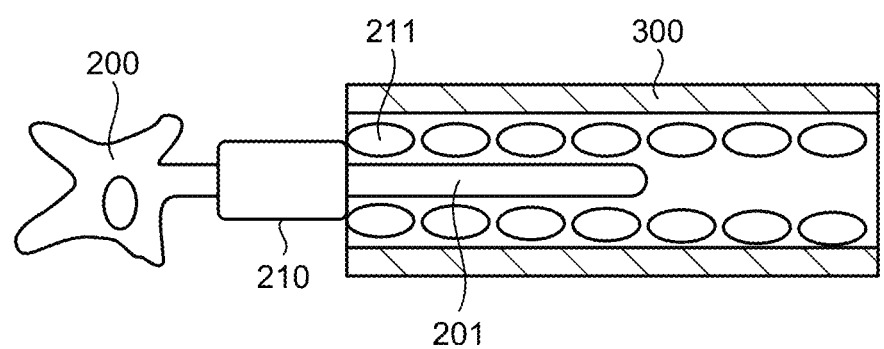
FIG. 15 is a view illustrating a use example of a conventional nerve regeneration-inducing tube.

FIG. 13 is a graph illustrating the results of axon growth rate evaluation. (neurite outgrowth rate). FIG. 14 is a graph illustrating the results of axon growth linear extension evaluation. (aspect ratio). As can be understood from FIG. 13, it can be said that the neurite outgrowth rate in a case of the modified cross-section fibers having a substantially Y- or X-shaped cross section is higher than that in a case of the fibers having a substantially elliptical shape cross section. As can be understood from FIG. 14, it can be said that the aspect ratio in a case of the modified cross-section fibers having a substantially Y- or X-shaped cross section is higher than that in a case of the fibers having a substantially elliptical shape cross section and that the linear extension degree of axon growth is high.

INDUSTRIAL APPLICABILITY

According to the nerve regeneration-inducing tube of the present invention, the extension of an axon can be improved. Therefore, the present invention is industrially very applicable since efficient nerve regeneration can be achieved.

REFERENCE SIGNS LIST

1 Nerve regeneration-inducing tube
10 Body
11, 11A Modified cross-section fiber
110, 120 Axis
111, 121 Protrusion

The invention claimed is:

1. A nerve regeneration-inducing tube comprising:
a cylindrical body; and
a plurality of fibers that are housed in the body and extend in a longitudinal direction of the body, wherein
at least a part of the fibers is a modified cross-section fiber that has
an axis extending in a longitudinal direction of the fibers, and
at least three protrusions that continue in the longitudinal direction of the fibers, protrude from the axis, and have a height of 0.5 μm or more from the axis.

2. The nerve regeneration-inducing tube according to claim 1, wherein in a cross section of the modified cross-section fiber, a modification degree that is a ratio of a diameter of a circle circumscribed to the cross section to a diameter of a circle inscribed to the cross section is 1.5 to 12.0.

3. The nerve regeneration-inducing tube according to claim 1, wherein the protrusions have a height of 1.0 μm or more.

4. The nerve regeneration-inducing tube according to claim 1, wherein the modified cross-section fiber has 10 or less of the protrusions.

5. The nerve regeneration-inducing tube according to claim 4, wherein the modified cross-section fiber has a Y-cross-section fiber having three of the protrusions or an X-cross-section fiber having four of the protrusions.

6. The nerve regeneration-inducing tube according to claim 1, wherein the fibers include fibers having different cross-sectional shapes.

7. The nerve regeneration-inducing tube according to claim 1, wherein at least one of the body and the fibers includes a bioabsorbable polymer.

* * * * *